United States Patent [19]

Trygstad et al.

[11] Patent Number: 4,596,790
[45] Date of Patent: Jun. 24, 1986

[54] PEPTIDES FOR THE TREATMENT OF HYPERGLYCAEMIA

[75] Inventors: Olav E. Trygstad, Haslum; Karl-Ludwig Reichelt, Oslo; Kirsten Titlestad, Stend, all of Norway

[73] Assignee: Nyegaard & Co. A/S, Olso, Norway

[21] Appl. No.: 662,060

[22] Filed: Oct. 18, 1984

[30] Foreign Application Priority Data

Oct. 19, 1983 [GB] United Kingdom ............... 8327966

[51] Int. Cl.$^4$ ........................ A61K 37/24; C07K 5/10
[52] U.S. Cl. ...................................... 514/18; 530/330
[58] Field of Search .................... 260/112.5 R; 514/18

[56] References Cited

U.S. PATENT DOCUMENTS 4,353,823 10/1982 Chipens et al. ............. 260/112.5 R
4,409,141 10/1983 Noda et al. ................. 260/112.5 R
4,410,514 10/1983 Vale, Jr. et al. ............. 260/112.5 R Primary Examiner—Delbert R. Phillips
Attorney, Agent, or Firm—Bacon & Thomas

[57] ABSTRACT

Peptides of formula I pGlu-X-Asp-Gly    (I)

(where X is Glu, Asp or Gln, and Gly, pGlu, Glu, Gln and Asp represent residues of glycine and L-forms of pyroglutamic acid, glutamic acid, glutamine and aspartic acid respectively) and/or physiologically acceptable salts thereof are disclosed together with a process for their preparation. The compounds may be used in the treatment of hyperglycaemia, and pharmaceutical compositions comprising as active ingredient at least one compound of formula I are also disclosed.

7 Claims, No Drawings

PEPTIDES FOR THE TREATMENT OF HYPERGLYCAEMIA

The present invention relates to novel peptides effective in controlling release of insulin.

The mechanism for control of glucose in the body to within permitted levels of tolerance involves the release of insulin from the pancreatic β-cells when extracellular glucose concentrations are elevated. It is essential that this response is sensitive to relatively small changes in glucose concentration and reduction of this sensitivity results in deterioration of glucose tolerance and, if sufficiently pronounced, in diabetes mellitus. Most forms of diabetes are, in fact, caused by a secretory defect in the pancreatic β-cells.

Glucose is not the only stimulus for insulin secretion. A wide variety of agents including other sugars, amino acids, hormones and pharmacological substances can influence the secretory activity of the pancreatic activity of the pancreatic β-cells. The stimulatory compounds are either referred to as initiators, capable of eliciting insulin release by themselves, or potentiators which can only increase the secretory response revoked by an initiator. The interaction of the various stimuli with the β-cell involves their recognition, followed by coupling of the stimulatory signal to the discharge of insulin which occurs by exocytosis.

Sulphonylurea compounds have been used in the diabetes therapy for more than 25 years essentially due to their ability to stimulate the secretory activity of the pancreatic β-cells (Mentellen Pharmakologie 32/2, pp. 175–194, G. M. Grodsky, G. H. Epstein, R. Fanska and B. Hellman. *Acta Biol. Med. Germ.* 41,1211, 1982). It has, however, been suggested that long-term treatment with sulphonylureas results in an increased mortality in vascular diseases.

A more significant disadvantage is that the sulphonylurea action on insulin release is not restricted to potentiation of the glucose effect so that serious hypoglycaemic reactions can occur during treatment of diabetes with sulphonylureas.

A number of substances isolated from the urine or gastro-intestinal tract of patients having irregular glucose and/or insulin metabolism and from other sources have been reported as having hypoglycaemic effects. Some of these have been peptides, for example gastric inhibitory polypeptide (GIP), glucetin and a heptacosapeptide isolated from porcine intestine. These have all been relatively long peptides; for example GIP has 42 amino acid units and the heptacosapeptide clearly has 27.

A so-called lipodystrophy factor has been isolated from the urine of lipodysotrophic patients and was found to induce lipodystrophy in mice. One symptom of lipodystrophy is excessive insulin activity. The lipodystrophy factor, as described in the literature, was a heterogeneous mixture of active substances having different physiological actions.

One substance isolated from this mixture was reported as having hyperglycaemic and hyperinsulinaemic activity and possessed the structure pGlu-Ser-Asp-Gly.

We have now isolated from the above lipodystrophy factor a further tetrapeptide which possesses the ability to potentiate the insulin releasing activity of glucose and which contains the residues of the amino acids pyroglutamic acid, glutamic acid or glutamine, aspartic acid or asparagine and glycine.

Thus, by separating this hypoglycaemic tetrapeptide from the hyperglycaemic substances and other highly active factors present in the above lipodystrophy factor, we have made available a valuable therapeutic agent for use in the treatment of diabetes mellitus and other hyperglycaemic conditions.

Although the exact structure of the natural peptide has yet to be determined, we have prepared, by total synthesis, a small group of related peptides which we have shown to possess similar insulin releasing properties.

It is particularly noteworthy that the potentiating effect is only active at relatively high glucose levels and there is consequently no danger that glucose concentrations will be reduced to dangerously low levels. The novel peptides are thus effective in simply normalising glucose concentrations without the risk of hypoglycaemia attendant in sulphonylurea therapy.

According to the present invention we provide novel peptides of the general formula (I)

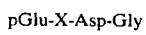

pGlu-X-Asp-Gly    (I)

(where X is Glu, Asp or Gln)
and physiologically acceptable salts thereof.

Physiologically acceptable salts of the compounds of formula (1) include salts with bases such as alkali metal salts, e.g. sodium or potassium salts, alkaline earth metal salts, e.g. calcium salts, or amine salts e.g. ethanolamine or arginine salts.

Especially active compounds according to the invention include p-Glu-Glu-Asp-Gly, p-Glu-Asp-Asp-Gly and in particular p-Glu-Gln-Asp-Gly, which is the most active of the compounds which we have prepared. In these formulae, Gly,pGlu,Glu,Gln and Asp symbols have their conventional meanings and represent glycine and L-forms of pyroglutamic acid, glutamic acid, glutamine and aspartic acid respectively.

As far as we are aware, the substances of formula (I), apart from the above-described tetrapeptide which occurs in nature (together with other peptides such as the above-mentioned pGlu-Ser-Asp-Gly), are all novel compounds. In any case, none of the substances of formula (I) has previously been obtained by synthesis or in pure or crystalline form.

The compounds of formula (I) are relatively stable in solution, with virtually no adsorption onto glass. They are orally active and substantially non-toxic. As indicated above, they do not induce hypoglycaemia, so that there is no risk of overdosage. They have a short half-life as compared with sulphonylureas, and a correspondingly short insulin-releasing action which enables them to be given immediately before a meal for control of glucose deriving from that meal. The peptides of formula (I), being short, have the further advantage of being readily prepared at low cost by total synthesis.

According to a still further feature of the present invention there are provided pharmaceutical compositions comprising as active ingredient at least one compound of formula (I) as hereinbefore defined or a physiologically compatible salt thereof, in association with a pharmaceutical carrier or excipient. The compositions according to the invention may be presented, for example, in a form suitable for oral, nasal, parenteral or rectal administration.

As used herein, the term "pharmaceutical" includes veterinary applications of the invention.

The compounds according to the invention may be presented in the conventional pharmacological forms of administration, such as tablets, coated tablets, nasal sprays, solutions, emulsions, powders, capsules or sustained release forms. Conventional pharmaceutical excipients as well as the usual methods of production may be employed for the preparation of these forms. Tablets may be produced, for example, by mixing the active ingredient or ingredients with known excipients, such as for example with diluents, such as calcium carbonate, calcium phosphate or lactose, disintegrants such as corn starch or alginic acid, binders such as starch or gelatin, lubricants such as magnesium stearate or talcum, and/or agents for obtaining sustained release, such as carboxypolymethylene, carboxymethyl cellulose, cellulose acetate phthalate, or polyvinylacetate.

The tablets may if desired consist of several layers. Coated tablets may be produced by coating cores, obtained in a similar manner to the tablets, with agent commonly used for tablet coatings, for example, polyvinyl pyrrolidone or shellac, gum arabic, talcum, titanium, dioxide or sugar. In order to obtain sustained release or to avoid incompatibilities, the core may consist of several layers too. The tablet-coat may also consist of several layers in order to obtain sustained release, in which case the excipients mentioned above for tablets may be used.

Injection solutions may, for example, be produced in the conventional manner, such as by the addition of preservation agents, such as p-hydroxybenzoates, or stabilizers, such as EDTA. The solutions are then filled into injection vials or ampoules.

Nasal sprays may be formulated similarly in aqueous solution and packed into spray containers either with an aerosol propelllant or provided with means for manual compression. Capsules containing one or several active ingredients may be produced, for example, by mixing the active ingredients with inert carriers, such as lactose or sorbitol, and filling the mixture into gelatin capsules.

Suitable suppositories may, for example, be produced by mixing the active ingredient or active ingredient combinations with the conventional carriers envisaged for this purpose, such as natural fats or polyethyleneglycol or derivatives thereof. We have found that 4.4 mg of active peptide per kg bodyweight can substantially normalise glucose levels as high as 15 mmol/liter in serum. For adult humans, a preferred dose level before meals is in the range 100 mg to 500 mg, preferably 200 mg to 400 mg. Dosage units containing such amounts of active substance per dose are thus convenient.

According to a still further feature of the present invention there is provided a method of combating hyperglycaemia in warm-blooded animals including humans which comprises administering an effective amount of a pharmaceutical composition as hereinbefore defined to a subject suffering from hyperglycaemia whereby extracellular glucose levels are reduced.

A further major use of the new peptides, however, is in the production of material for immunological assay techniques. The peptide may then be covalently attached to a suitable high molecular carrier such as albumin, polysine or polyproline in order to be injected into antibody-producing animals (e.g. rabbits, guinea pigs or goats). High specificity antisera are obtained by use of well known absorption techniques, using the high molecular carrier. By introducing radioactivity ($^{14}C$, $^{3}H$, $^{18}O$, $^{15}N$) into the peptide molecule, a radioimmuno assay can readily be designed and used for determining the peptide in the different biological fluids such as serum (plasma), urine and cerebrospinal fluid.

The peptides of the invention may be synthesised in any convenient way. In general, the reactive groups present (amino and/or carboxyl) will be protected during the overall synthesis and the final stage will thus be the deprotection of a protected derivative of formula (I) or a salt thereof. Normally, all —COOH groups, all —NH$_2$ groups and the —NH group of the p-Glu residue will be protected.

A wide choice of protecting groups for amino-acids are known and are exemplified in Schröder, E., and Lübke, K., The Peptides, Vols. 1 and 2, Academic Press, New York and London, 1965 and 1966; Pettit, G. R., Synthetic Peptides, Vols. 1-4, Van Nostrand, Reinhold, New York 1970, 1971, 1975 and 1976, Houben-Weyl, Methoden der Organischen Chemie, Synthese von Peptiden, Band 15, Georg Thiene Verlag, Stuttgart 1974; and Amino Acids, Peptides and Proteins, Vol. 4-8, The Chemical Society, London 1972, 1974, 1975 and 1976.

Thus, for example amine protecting groups which may be employed include the carbobenzoxy (hereinafter also designated Z) trityl, methoxybenzhydryl (hereinafter designated Mbh)t-butoxycarbonyl (hereinafter also designated Boc) and acyl groups such as, for example, an acetyl group or a formyl group.

Carboxyl-protecting groups which may, for example be employed include readily cleaved ester groups such as benzyl (hereinafter also designated Bzl), Mbh, p-nitrobenzyl or t-butyl groups.

It will be appreciated that a wide range of other such groups exists as, for example, detailed in the above-mentioned literature references, and the use of all such groups in the hereinbefore described processes fall within the scope of the present invention.

Carboxyl protecting groups may be introduced by conventional methods e.g. by reaction with a suitable esterifying reagent, for example an alcohol such as benzyl or p-nitrobenzyl alcohol in the presence of acid, e.g. p-toluenesulphonic acid.

Amine-protecting groups may be introduced by conventional methods e.g. by reaction with suitable acid halides such as carbobenzoxy chloride or pivaloyl chloride, or acid anhydrides such as acetic anhydride.

A wide range of procedures exists for removing amine- and carboxyl-protecting groups. Thus, for example an amine-protecting group may be removed by acidolysis, hydrogenolysis, treatment with dilute ammonium hydroxide, treatment with sodium, treatment with sodium amide, treatment with hydrazine, or enzymatic hydrolysis with, for example, leucineaminopeptidase. Methods which are of interest also include treatment with anhydrous hydrogen bromide for example in glacial acetic acid, treatment with trifluoroacetic acid and catalytic hydrogenation.

Thus carbobenzoxy and t-butoxy carbonyl groups may be removed, for example, using anhydrous hydrogen bromide conveniently in the presence of glacial acid or using trifluoroacetic acid conveniently in the presence of concentrated hydrochloric acid; acyl groups may for example be removed by conventional hydrolysis with acid or by enzymatic hydrolysis as described above.

The removal of carboxyl-protecting groups may, for example, be effected by saponification, acidolysis, hydrogenolysis or enzymatic hydrolysis. Thus, for example, saponification may be effected with an alkali metal hydroxide conveniently in the presence of water, an alcohol and/or acetone. Acidolysis may, for example, be effected by the use of anhydrous hydrogen bromide or trifluoroacetic acid and hydrogenolysis may, for example be effected by catalytic hydrogenation e.g. by the use of palladium on carbon, conveniently 10% palladium on charcoal. Enzymatic hydrolysis may, for example, be effected by the use of leucineaminopeptidase. Thus, for example, benzyl and p-nitrobenzyl groups may be removed by hydrogenolysis and t-butyl groups may, for example, be removed by saponification.

Amine-hydroxyl and carboxyl-protecting groups may, for example, be removed simultaneously by acidolysis, alkaline hydrolysis, hydrogenolysis, treatment with sodium or sodium amide or by enzymatic hydrolysis. Such methods include treatment with hydrogen bromide, conveniently in the presence of glacial acetic acid, and treatment with alcohol conveniently containing dissolved dry hydrogen chloride.

One method of selective deprotection is, for example, catalytic hydrogenation, conveniently using palladium on, for example, carbon as the catalyst and conveniently in the presence of a solvent e.g. water, methanol, dioxan, acetic acid or t-butanol. This method removes, for example, the carbobenzoxy group, but leaves the t-butoxycarbonyl or an acyl group intact.

In general, the protected derivatives of the compounds of formula (I) can be prepared by coupling together the required amino acids in suitably protected form using the techniques appropriate for peptide synthesis. One can start at the C-terminal by reaction of a suitably protected derivative of glycine with a suitably protected derivative of aspartic acid. The glycine derivative will have a free amino group while the other reactant will have either a free or activated carboxyl group and a protected amino group. After coupling the intermediate may be purified, for example by chromatography, and then N-deprotected to permit addition of a further amino acid residue. This procedure is continued until the required amino acid sequence is completed. N-deprotection will normally be effected by mild acidolysis; the excess acid is normally neutralised before the next coupling step, e.g. using a base such as triethylamine.

Alternatively, it is possible to start at the N-terminal and react a suitably protected pyroglutamic acid derivative, preferably having an activated carboxyl group, with a suitably protected derivatives of either glutamic acid, aspartic acid or glutamine. After coupling, the product may be purified e.g. by chromatography, and the terminal α-carboxyl group deprotected and, if desired, activated, prior to the next coupling step. This sequence of steps is repeated until the desired peptide is complete.

Carboxylic acid activating substituents which may, for example, be employed include mixed anhydrides, azides or activated esters such as for example p-nitrophenyl ester, 2,4,5-trichlorophenyl ester, N-hydroxybenzotriazole ester, or N-hydroxysuccinimidyl ester.

In general it is convenient to effect the coupling reactions at low temperatures, for example, −20° C. up to ambient temperature, conveniently in a suitable solvent system, for example, tetrahydrofuran, dioxan, dimethylformamide, methylene chloride or a mixture of these solvents.

The coupling of free amino and carboxyl groups may, for example, be effected using dicyclohexylcarbodiimide (DCC). Another coupling agent which may, for example, be employed is N-ethoxycarbonyl-2-ethoxy-1,2-dihydroquinoline.

It may be more convenient to carry out the synthesis on a solid phase resin support. Chloromethylated polystyrene (cross-linked with 1% divinyl benzene) is one useful type of support; in this case the synthesis will start at the C-terminal by coupling glycine to the support. Where X is to be other than OH, the terminal α-carbonyl group formed on clearing the peptide from the support may be reacted further to introduce the desired groupings.

The following Examples, which are of a non-limiting nature, illustrate the synthesis of the insulin-releasing tetrapeptide L-(pyro)glutamyl-L-glutamyl (γ—OH)-L-aspartyl(β—OH)-glycine and of two analogues to this peptide.

In the Examples the following abbreviations are used:
Boc—tert-butoxycarbonyl
DCC—dicyclohexylcarbodiimide
DCU—dicyclohexylurea
N-HOSu—N-hydroxysuccinimide
Mbh—Dimethoxybenzhydryl
OBu$^t$—t-butoxy
OBzl—benzoxy
Pet. ether—Light petroleum (b.p. 40°-60° C.)
TFA—trifluoroacetate
THF—tetrahydrofuran
Tos—p-toluene sulphonic acid
mM—mmol Five TLC systems were used for product analysis:

| | | |
|---|---|---|
| S$_1$:Silica gel 60 F$_{254}$ | | CHCl$_3$:MeOH (2:98) |
| S$_2$:Silica gel 60 F$_{254}$ | | CHCl$_3$:MeOH (5:95) |
| S$_3$:Silica gel 60 F$_{254}$ | Silanized | MeOH:H$_2$O (70:30) |
| S$_4$:Silica gel 60 F$_{254}$ | | EtOH:H$_2$O (70:30) |
| S$_5$:Silica gel 60 F$_{254}$ | | CHCl$_3$:MeOH (90:10) |

Detection of the spots on the TLC-plates was done by (1) UV-light (254 nm) and (2) treating the plates with Cl$_2$ for 10–15 min followed by spraying with a solution made of 100 mg dicarboxidine, 0.5 g KI and 15 ml glacial acetic acid diluted to 100 ml with H$_2$O.

Ion-exchanged water was used in all the procedures involving use of water.

EXAMPLE 1

H-L-(PYRO) GLUTAMYL-L-GLUTAMYL-L-ASPARTYL-GLYCINE

H-L-pGlu-L-Glu-L-Asp-Gly-OH (a) tert-Butoxycarbonyl-L-aspartyl(β-benzyl ester)glycine benzyl ester (Boc-L-Asp(β-OBzl)-Gly-OBzl)

1. Tos.H-Gly-OBzl: (9.9 g, 30 mM) was dissolved in 30 ml CH$_2$Cl$_2$ and
2. Boc-L-Asp(β-OBzl)-OH: (8.73 g, 30 mM),
3. N-Ethylmorpholine: (3.6 g, 30 mM),
4. N-HOSu: (7.5 g, 60 mM)

were added successively with stirring. The reaction mixture was cooled to −20° C. in a thermostated bath 5. DCC: (6.9 g, 33 mM) dissolved in 20 ml CH$_2$Cl$_2$ was added dropwise with stirring.

The temperature was raised with 0.024° C./min overnight with a gradient-controlled thermostat. DCU was filtered and washed with the solvent and the combined solvent was evaporated in vacuo. The residue was redissolved in 200 ml ethylacetate and washed successively with 2×50 ml 0.1 M HCl
2×50 ml 1 M NaHCO$_3$
2×50 ml 1 M NaCl and filtered through a phase separation paper and the solvent evaporated in vacuo.

The resulting pale yellow oil was crystallized from diethylether/pentane (refrigerator). The white crystalline solid was dried over P$_2$O$_5$. TLC (S$_1$) showed one major product. The solid was used without further purification.

0.25 g of solid was dissolved in 0.8 ml methanol and purified on a silica gel 60 silarized column eluted with 70% methanol in water. 2.2 ml fractions were collected by a fraction collector. The combined fractions containing pure product (by TLC) were evaporated to dryness (in vacuo). The product was recrystallized from diethylether/pentane (refrigerator) and dried over P$_2$O$_5$. The white solid was homogeneous on TLC. R$_f$-values: 0.506 (S$_1$), 0.764(S$_2$), 0.592 (S$_3$).

Melting point: 72° C.

(b) H-L-aspartyl($\beta$-benzyl ester)-glycine benzyl ester) Trifluoroacetate (TFA.H-L-Asp($\beta$-OBzl)-Gly-OBzl)

Boc-1-Asp($\beta$-OBZl)-Gly-OBzl (4.7 g, 10 mM) was dissolved in 15 ml trifluoroacetic acid. The reaction mixture was stirred at ambient temperature until TLC showed that all starting material was consumed. The solvent was removed in vacuo. NMR ($^1$H) showed that the Boc-group was removed. The product was used without further treatment.

(c) tert-Butoxycarbonyl-L-glutamyl($\gamma$-benzyl ester)-L-aspartyl($\beta$-benzyl ester)-glycine benzyl ester Boc-L-Glu($\gamma$-OBzl)-L-Asp($\beta$-OBzl)-Gly-OBzl 1. TFA.H-L-Asp($\beta$-OBzl)-Gly-OBzl: (4.8 g, 10 mM) was dissolved in 15 ml CH$_2$Cl$_2$ and
2. Boc-L-Glu-($\gamma$-OBzl)-OH: (3.38 g, 10 mM),
3. N-Ethylmorpholine: (1.2 g, 10 mM),
4. N-HOSu: (2.3 g, 20 mM)

were added successively with stirring.

The reaction mixture was cooled to −20° C. in a thermostated bath.

5. DCC: (2.27 g, 11 mM)

dissolved in 10 ml CH$_2$Cl$_2$
was added dropwise with stirring. The temperature was raised with 0.024° C./min overnight with a gradient-controlled thermostat. DCU was filtered and washed with the solvent, and the combined solvent was evaporated in vacuo. The residue was redissolved in 100 ml ethylacetate and washed successively with:

2×20 ml 0.1 M HCl
2×20 ml 1 M NaHCO$_3$
2×20 ml 1 M NaCl and filtered through a phase separation paper, and the solvent was evaporated in vacuo.

The resulting brown oil was crystallized from MeOH/diethylether and pentane (refrigerator). The white crystalline solid was dried over P$_2$O$_5$. TLC (S$_1$) showed one major product.

The solid was used without further purification.

0.3 g of the solid was dissolved in 1 ml CHCl$_3$:MeOH (98:2) and purified on a silica gel 60 column eluted with CHCl$_3$:MeOH (98:2). 2.5 ml fractions were collected by a fraction collector. The combined fractions containing pure product (by TLC) were evaporated to dryness (in vacuo). The product was recrystallized from CHCl$_3$/diethylether (refrigerator) and dried over P$_2$O$_5$. The white solid was homogeneous on TLC. R$_f$-values: 0.411 (S$_1$), 0.686 (S$_2$), 0.317 (S$_3$).

M.p: 101.5°–102° C.

(d) H-L-glutamyl($\gamma$-benzyl ester)-L-aspartyl ($\beta$-benzyl ester)-glycine benzyl ester Trifluoroacetate TFA.H-L-Glu($\gamma$-OBzl)-L-Asp($\beta$-OBzl)-Gly-OBzl BOC-L-Glu($\gamma$-OBzl)-L-Asp($\beta$-Obzl)-Gly-OBzl (4.4 g, 6.4 mM) was dissolved in 15 ml trifluoroacetic acid. The reaction mixture was stirred at ambient temperature until TLC showed that all starting material was used up. The solvent was removed in vacuo. NMR ($^1$H) showed that the Boc-group was removed. The product was used without further treatment.

(e) Carbobenzoxy-L-(pyro)glutamyl-L-glutamyl($\gamma$-benzyl ester)-L-aspartyl($\beta$-benzyl ester)-glycine-benzyl ester Z-L-pGlu-L-Glu($\gamma$-OBzl)-L-Asp($\beta$-OBzl)-Gly-OBzl 1. TFA.H-L-Glu($\gamma$-OBzl)-L-Asp($\beta$-OBzl)-Gly-OBzl: (4.5 g, 6.4 mM)

was dissolved in 10 ml CH$_2$Cl$_2$ and

2. Z-L-pGlu-OH: (1.69 g, 6.4 mM),
3. N-Ethylmorpholine: (0.74 g, 6.4 mM)
4. N-HOSu: (1.47 g, 12.8 mM)

were added successively with stirring. The reaction mixture was cooled to −20° C. in a thermostated bath.

5. DCC: (1.45 g, 7 mM) dissolved in 7.5 ml CH$_2$Cl$_2$ was added dropwise with stirring. The temperature was raised with 0.024° C./min overnight with a gradient-controlled thermostat. DCU was filtered off and washed with the solvent, and the combined solvent was evaporated in vacuo. The residue was redissolved in 175 ml ethylacetate and washed successively with:

2×40 ml 0.1 M HCl
2×40 ml 1 M NaHCO$_3$
2×40 ml 1 M NaCl and filtered through a phase separation paper and the solvent evaporated in vacuo.

The resulting semicrystalline solid was crystallized from CHCl$_3$/MeOH (refrigerator). The white crystalline solid was dried over P$_2$O$_5$. TLC (S$_2$) showed one major product. The solid was used without further purification.

0.25 g of the solid was dissolved in 1 ml CHCl$_3$:MeOH (95:5) and purified on a silica gel 60 column eluted with CHCl$_3$:MeOH (95:5). 2.5 ml fractions were collected by a fraction collector. The combined fractions containing pure product (by TLC) were evaporated to dryness (in vacuo). The product was recrystallized from CHCl$_3$/diethylether (refrigerator) and dried over P$_2$O$_5$. The white solid was homogeneous on TLC. R$_f$-values: 0.888 (S$_1$), 0.357 (S$_2$), O (S$_3$).

M.p.: 163.5°–164° C.

(f) H-L-(pyro)glutamyl-L-glutamyl-L-aspartyl-glycine

H-L-pGlu-L-Glu-L-Asp-Gly-OH

Z-L-pGlu(-OBzl)-L-Asp($\beta$-OBzl)-Gly-OBzl (1 g 1.22 mM) was dissolved in 7.5 ml tetrahydrofuran and 0.5 ml $H_2O$ was added. The reaction vessel was flushed with $N_2$ and 10% Pd/C (150 mg) was added. $H_2$ was led through the stirred reaction mixture. During the first one and a half hours 7 ml $H_2O$ was added in 1 ml portions. The reaction was monitored on TLC, and when all starting material was consumed and the TLC picture was constant, the catalyst was removed by filtration, and the remainders of organic solvent were removed in vacuo. The aqueous solution was lyophilized. The lyophilized product was purified on the following chromatography systems (in the following order):

1. Silica Gel 60 silanized: $MeOH:H_2O$ (1:9) (column)
2. Sephadex G-10: $H_2O$ (column)
3. Fractogel PGM 2000: 0.2 M HCOOH (column)

The combined fractions which contain the product were lyophilized after each run (after evaporation of organic solvent if necessary). After this treatment the lyophilized product was homogeneous on TLC.

$R_f=0.634$ ($S_4$). Proton NMR is available.

EXAMPLE 2

H-L-(PYRO) GLUTAMYL-L-ASPARTYL-L-ASPARTYL-GLYCINE

H-L-pGlu-L-Asp-L-Asp-Gly-OH (a) tert-Butoxycarbonyl-L-aspartyl ($\beta$-benzyl ester)-L-aspartyl ($\beta$-benzyl ester)-glycine benzyl ester Boc-L-Asp($\beta$-OBzl)-L-Asp($\beta$-OBzl)-Gly-OBzl 1. TFA.H-L-Asp($\beta$-OBzl)-Gly-OBzl: (2.423 g, 5 mM)
was dissolved in 10 ml $CH_2Cl_2$ and
2. Boc-L-Asp($\beta$-OBzl)-OH: (1.62 g, 5 mM),
3. N-Ethylmorpholine: (0.6 g, 5 mM)
4. N-HOSu: (1.25 g, 10 mM)
were added successively with stirring.

The reaction mixture was cooled to $-20°$ C. in a thermostated bath.

5. DCC: (1.13 g, 5.5 mM)
dissolved in 6 ml $CH_2Cl_2$ was added dropwise with stirring. The temperature was raised with 0.024° C./min overnight with a gradient-controlled thermostat. DCU was filtered off and washed with the solvent, and the combined solvent was evaporated in vacuo. The residue was redissolved in 100 ml ethylacetate and washed successively with:

2×30 ml 0.01 M HCl
2×30 ml 1 M $NaHCO_3$
2×30 ml 1 M NaCl
and filtered through a phase separation paper and the solvent evaporated in vacuo.

The resulting yellow oil was crystallized from $CHCl_3$/diethylether and pentane (refrigerator). The white crystalline solid was dried over $P_2O_5$. TLC ($S_1$) showed one major product.

The solid was used without further purification. 0.10 g of the solid was recrystallized from MeOH/diethylether and pentane (refrigerator) and was dried over $P_2O_5$. The white solid was homogeneous on TLC. $R_f$ values: 0.40 ($S_1$), 0.544 ($S_2$).

(b) H-L-aspartyl ($\beta$-benzyl ester)-L-aspartyl($\beta$-benzyl ester)-glycine benzyl ester Trifluoroacetate
TFA.H-L-Asp($\beta$-OBzl)-L-Asp($\beta$-OBzl)Gly-OBzl Boc-L-Asp($\beta$-OBzl)-Gly-OBzl (1.82 g, 2.7 mM) was dissolved in 7 ml trifluoroacetic acid. The reaction mixture was stirred at ambient temperature until TLC showed that all starting material was consumed. The solvent was removed in vacuo. NMR ($^1H$) showed that the Boc-group was removed. The product was used without further treatment.

(c)

Carbobenzoxy-L-(pyro)glutamyl-L-aspartyl($\beta$-benzyl ester)-L-aspartyl-($\beta$-benzyl ester)-glycine benzyl ester Z-L-pGlu-L-Asp($\beta$-OBzl)-L-Asp($\beta$-OBzl)-Gly-OBzl 1. TFA.H-L-Asp($\beta$-OBzl)-L-Asp($\beta$-OBzl)-Gly-OBzl: (1.86 g, 2.7 mM)
was dissolved in 7 ml $CH_2Cl_2$ and
2. Z-l-pGlu-OH: (0.72 g, 2.7 mM),
3. N-Ethylmorpholine: (0.32 g, 2.7 mM),
4. N-HOSu: (0.62 g, 5.4 mM)
were added successively with stirring.

The reaction mixture was cooled to $-20°$ C. in a thermostated bath.

5. DCC: (0.62 g, 3 mM) dissolved
in 3 ml $CH_2Cl_2$ was added dropwise with stirring.
The temperature was raised with 0.024° C./min overnight with a gradient-controlled thermostat. DCU was filtered off and washed with the solvent, and the combined solvent was evaporated in vacuo. The residue was redissolved in 70 ml ethylacetate and washed successively with:

2×20 ml 0.1 M HCl
2×20 ml 1 M $NaHCO_3$
2×20 ml 1 M NaCl and filtered through a phase separation paper and the solvent evaporated in vacuo.

The resulting oil was crystallized from $CH_2Cl_2$/diethylether(refrigerator). The white crystalline solid was recrystallized from $CH_2Cl_2$/MeOH and dried over $P_2O_5$. The white solid was homogeneous on TLC. $R_f$ values: 0.078 ($S_1$), 0.306 ($S_2$), 0.306 ($S_2$).

M.p.: 158°–160° C.

(d) H-L-(pyro)glutamyl-L-aspartyl-L-aspartyl-glycine

H-L-pGlu-L-Asp-L-Asp-Gly-OH

Z-L-pGlu-L-Asp($\beta$-OBzl)-L-Asp($\beta$-OBzl)-Gly-OBzl (0.32 g, 0.4 mM) was dissolved in 5 ml tetrahydrofuran and 0.5 ml $H_2O$ was added. The reaction vessel was flushed with $N_2$ and 10% Pd/C (0.10 g) was added. $H_2$ was led through the stirred reaction mixture. During the first one and a half hours 4.5 ml $H_2O$ was added in 1.5 ml portions. The reaction was monitored on TLC, and when all starting material was consumed and the TLC picture constant, the catalyst was removed by filtration, and the remainders of organic solvent were removed in vacuo. The aqueous solution was lyophilized. The lyophilized product was homogeneous on TLC. $R_f=0.667$ ($S_4$).

EXAMPLE 3

H-L-(PYRO) GLUTAMYL-L-GLUTAMINYL-L-ASPARTYL-GLYCINE

H-L-pGlu-L-Gln-L-Asp-Gly-OH (a) tert Butoxycarbonyl-L-aspartyl ($\beta$-benzyl ester)-glycine benzyl ester Boc-L-Asp-($\beta$-OBzl)-Gly-OBzl 1. Tos.H-Gly-Obzl: (3.3 g, 10 mM)
2. N-Ethylmorpholine: (1.2 g, 10 mM)
3. Boc-L-Asp($\beta$-OBzl)-OH: (3.2 g, 10 mM)
4. N-HOSu: (2.5 g, 22 mM)

were dissolved in $CH_2Cl_2$, cooled to $-20°$ C. and

5. DCC: (2.3 g, 11 mM)

was added. The mixture was allowed to attain room temperature (15 hrs). The precipitated DCU was filtered off and the solution washed successively with
1. 0.1 M HCl
2. $H_2O$
3. 0.5 M $NaHCO_3$
4. $H_2O$ and dried over $MgSO_4$. After evaporation of the solvent the viscous oil was crystallised from ether/Pet. ether and dried.

The resulting solid (3.7 g, 79%) was homogeneous by TLC, $R_f$ values: 0.45 ($S_1$), 0.65 ($S_2$)

Melting point: 70° C.

(b) H-L-Aspartyl($\beta$-benzyl ester)-glycine benzyl ester Trifluoroacetate

TFA.H-L-Asp($\beta$-OBzl)-Gly-OBzl

Boc-L-Asp(OBzl)-Gly-OBzl (3.5 g, 7.46 mmol) was dissolved in $CH_2Cl_2$, TFA and kept at room temperature (1½ h). The solvent was evaporated and the residue treated with Pet.ether to yield a foam (3.2 g, 89%) which was used without further purification.

(c) tert-Butoxycarbonyl-L-glutaminyl-L-aspartyl($\beta$-benzyl ester)-glycine benzyl ester Boc-L-Gln-L-Asp($\beta$-OBzl)-Gly-OBzl 1. TFA.H-L-Asp($\beta$-OBzl)Gly-OBzl: (1.0 g, 2.0 mM)
2. N-Ethylmorpholine: (0.25 g, 2.1 mM)
3. Boc-L-Gln-OH: (0.52 g, 2.1 mM)
4. N-HOSu: (0.5 g, 3.5 mM)

were dissolved in $CH_2Cl_2$, cooled to $-20°$ C. and

5. DCC: (0.45 g, 2.2 mM) was added.

The reaction was worked up as in (a).

After solvent evaporation, the residue was crystallized from ether to yield a white solid (0.8 g, 67%), homogeneous by TLC. $R_f(S_5)$ 0.50

Melting point: 110° C.

(d) H-L-Glutaminyl-L-aspartyl($\beta$-benzyl ester)-glycine benzyl ester

Trifluoroacetate
TFA.H-L-Gln-L-Asp($\beta$-OBzl)-Gly-OBzl

Boc-L-Gln-L-Asp($\beta$-OBzl)-Gly-OBzl (0.4 g, 0.66 mmol) was treated with TFA as described previously. To the residue, after evaporation, was added ether and Pet. ether and the obtained solid (0.4 g, 98%) was used without further purification.

(e) Carbobenzoxy-L-(pyro)glutamyl-L-glutaminyl-L-aspartyl ($\beta$-benzyl ester)-glycine-benzyl ester Z-L-pGlu-L-Gln-L-Asp($\beta$-OBzl)-Gly-OBzl 1. TFA H-L-Gln-L-Asp($\beta$-OBzl)-Gly-OBzl: (0.4 g, 0.66 mM)
2. N-Ethylmorpholine: (0.1 g, 0.8 mM)
3. Z-L-pGlu-OH: (0.18 g, 0.65 mM)
4. N-HOSu: (0.1 g, 0.86 mM)

was dissolved in $CHCl_2$, cooled to $-20°$ C. and

5. DCC: (0.15 g, 0.8 mM)

was added.

The mixture was stirred and allowed to attain room temperature (15 hrs). The precipitate containing DCU and the desired tetrapeptide was filtered off and dissolved in DMF. After filtration of insoluble DCU the solution was evaporated and the residue treated with $CH_2Cl_2$ and ether.

The resulting solid (0.45 g, 73%) was homogeneous by TLC, $R_f$ 0.4 ($S_5$)

Melting point: 175° C.

(f) H-L-(Pyro)Glutamyl-L-Glutaminyl-L-Aspartyl-Glycine

H-L-pGlu-L-Gln-L-Asp-Gly-OH

Z-L-pGlu-L-Asp(OBzl)-Gly-OBzl (0.12 g, 0.16 mmol) was dissolved in $THF/H_2O$, 5% Pd-C (0.2 g) added and hydrogen passed through the solution during 3 h. After filtration and evaporation, the residue was treated with THF to yield 0.07 g.

TLC showed one main product with a minor impurity. The tetrapeptide was obtained by further purification on a PGM 2000 column, eluting with formic acid (0.2 M). The resulting solid (0.05 g, 74%) was homogeneous by TLC. Rf 0.70 ($S_4$)

Melting point: 119° C.

We claim:

1. A peptide of formula I pGlu-X-Asp-Gly  (I)

(where X is Glu, Asp or GLn, and Gly, pGlu, Glu, Gln and Asp represent residues of glycine and L-forms of pyroglutamic acid, glutamic acid, glutamine and aspartic acid respectively) and/or physiologically acceptable salts thereof.

2. A peptide as claimed in claim 1 in crystalline form.

3. Pharmaceutical compositions for the treatment of hyperglycaemia in warm-blooded animals comprising an effective amount of an active ingredient for treating hyperglycaemia, and wherein said active ingredient is at least one compound as defined in claim 1 in association with a pharmaceutical carrier or excipient.

4. Compositions as claimed in claim 3 containing 100 mg to 500 mg of a compound as claimed in claim 1.

5. A method of combatting hyperglycaemia in warm-blooded animals including humans which comprises administering an effective amount of a pharmaceutical composition as defined in claim 3 to a subject suffering from hyperglycaemia whereby extra cellular glucose levels are reduced.

6. A pharmaceutical composition as claimed in claim 3, wherein the warm-blooded animals are humans.

7. A method of combatting hyperglycaemia as claimed in claim 5 wherein the warm-blooded animals are humans.

* * * * *